United States Patent [19]

Pelta

[11] Patent Number: 4,993,862
[45] Date of Patent: Feb. 19, 1991

[54] CLAMP ASSEMBLY FOR SURGICAL RETRACTOR SUPPORT

[75] Inventor: Samuel Pelta, Philadelphia, Pa.

[73] Assignee: Pilling Company, Fort Washington, Pa.

[21] Appl. No.: 394,673

[22] Filed: Aug. 16, 1989

[51] Int. Cl.⁵ .............................................. F16B 7/04
[52] U.S. Cl. ...................................... 403/59; 403/96; 403/391
[58] Field of Search ............... 403/92, 391, 389, 59, 403/97, 96, 55, 396, 390, 373; 128/20; 269/328, 235

[56] References Cited

U.S. PATENT DOCUMENTS

| | | | |
|---|---|---|---|
| 369,143 | 8/1887 | White | 403/55 |
| 1,469,448 | 10/1923 | Seavey | 403/55 |
| 3,357,726 | 12/1967 | Gabrielson | 403/59 |
| 4,339,844 | 7/1982 | Shatters | 403/96 X |
| 4,426,071 | 1/1984 | Klevstad | 269/328 X |
| 4,617,916 | 10/1986 | Le Vahn et al. | 269/328 X |
| 4,747,569 | 5/1988 | Hoshino | 403/97 X |

FOREIGN PATENT DOCUMENTS 630409 10/1949 United Kingdom ............... 403/391

Primary Examiner—Peter M. Cuomo
Attorney, Agent, or Firm—Howson & Howson

[57] ABSTRACT

A clamp assembly suitable for simultaneously adjusting the positions of support rods on an operating table extension in a split wishbone surgical retractor apparatus. Two independently rotatable disks are coaxially stacked on a base and tightened together by a bolt and T-shaped fitting extending through central openings of the base and disks. Channels formed between the disks and the base loosely receive the rods, and aligned bores in the base and the fitting loosely receive the extension. As the bolt and fitting are tightened, the rods and extension are clamped in fixed relative positions. The disks are interlocked at discrete angular positions by a pin and holes for adjusting the spread between the rods.

13 Claims, 3 Drawing Sheets

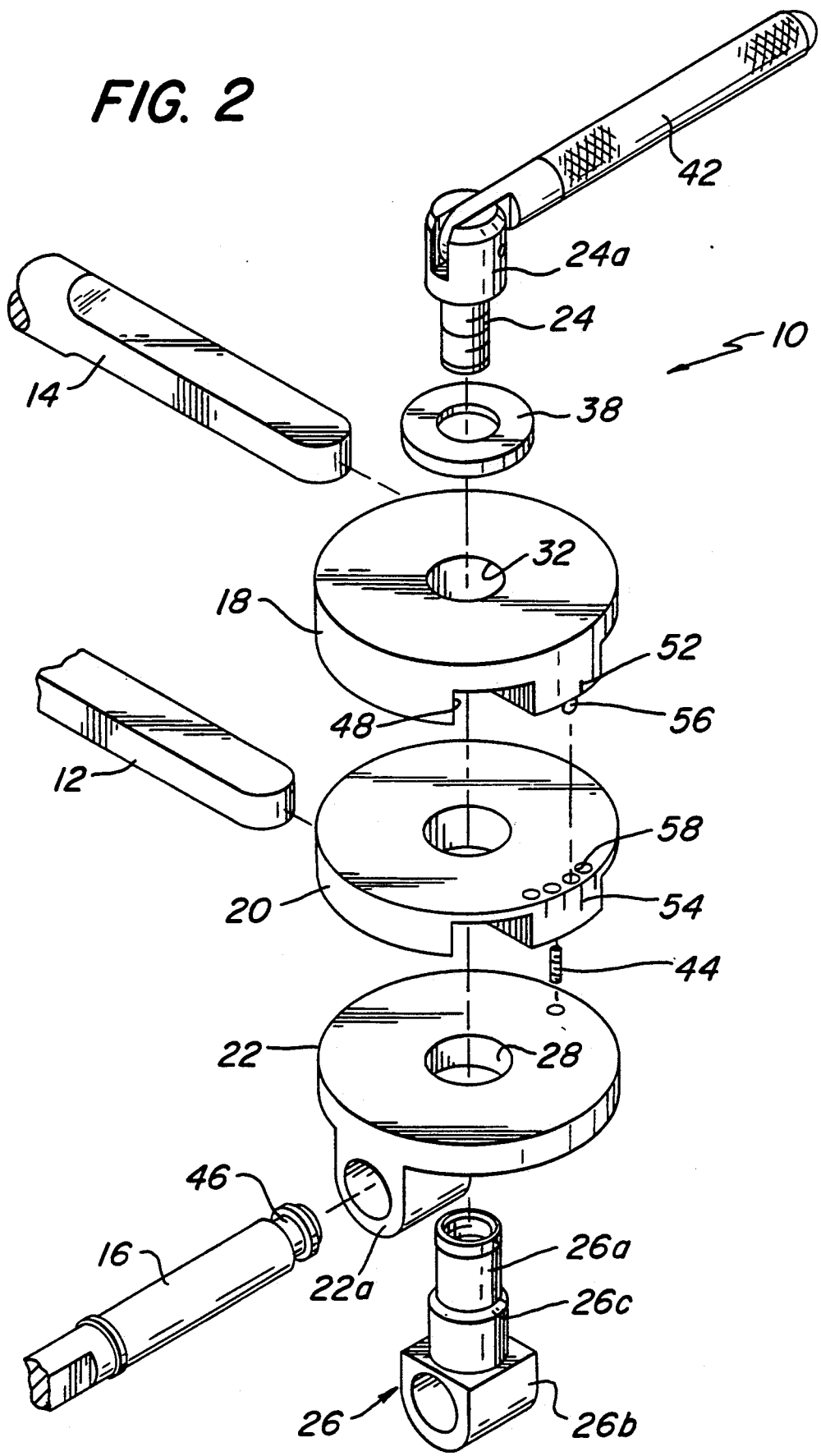

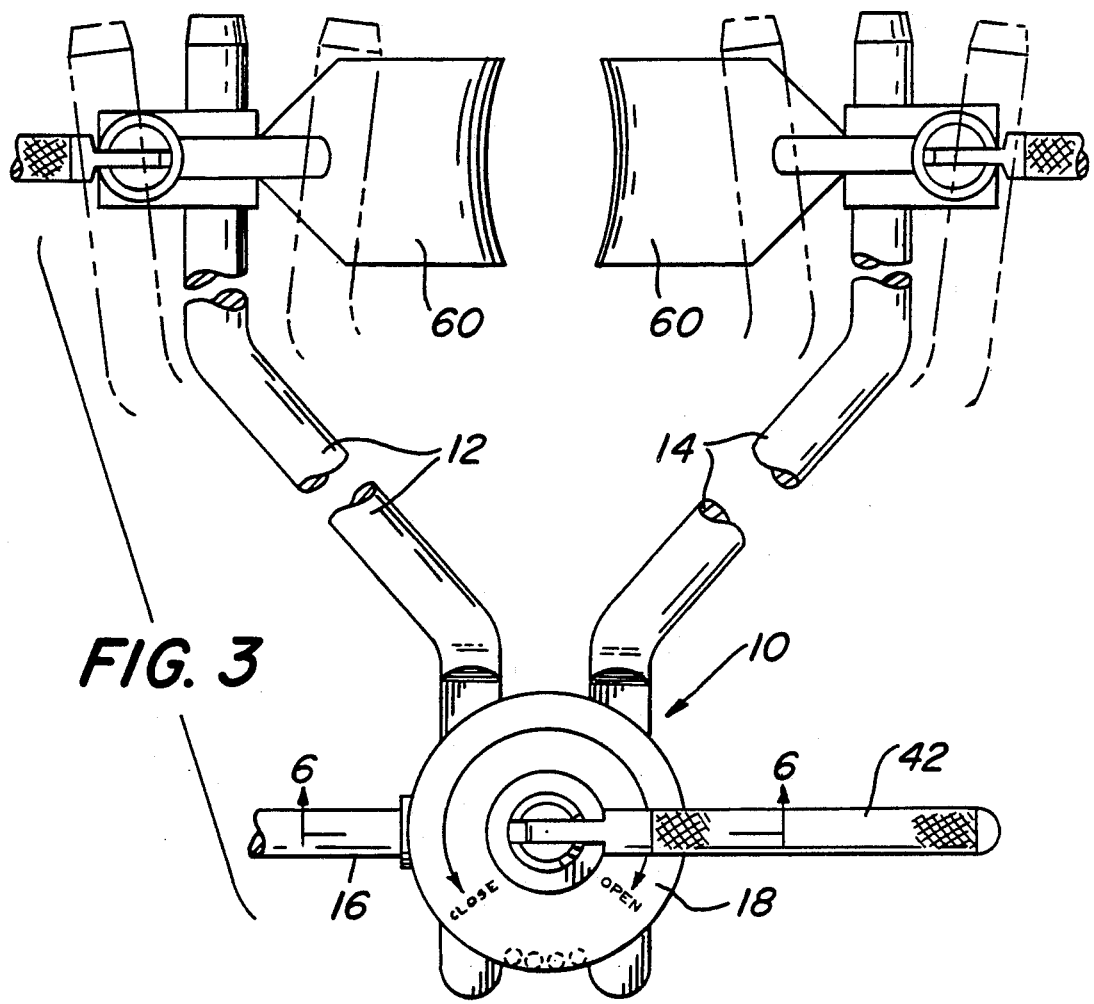
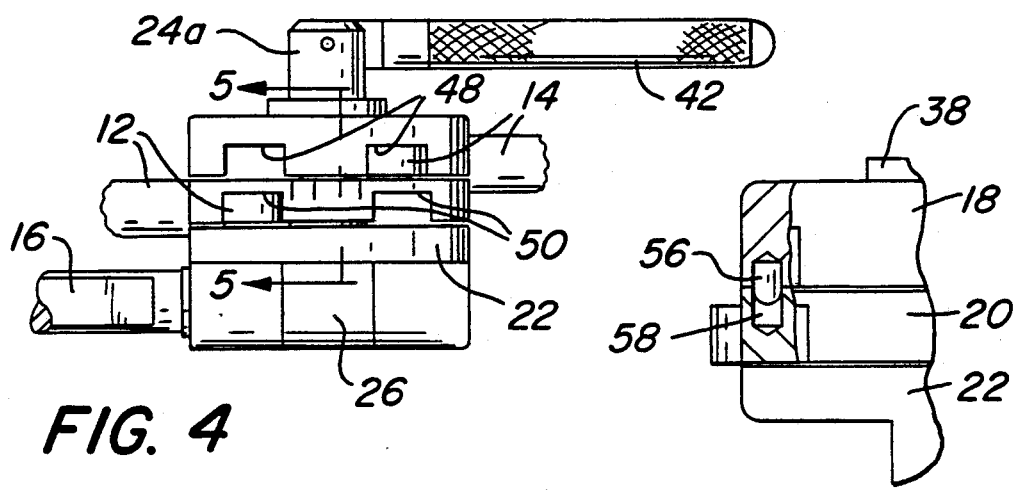

CLAMP ASSEMBLY FOR SURGICAL RETRACTOR SUPPORT

BACKGROUND OF THE INVENTION

The present invention relates generally to a table-mounted surgical retractor apparatus, and more particularly to an improved clamp assembly suitable for adjusting the spread between support rods to which surgical retractors are attached.

Surgical retractor apparatus such as disclosed in U.S. Pat. No. 4,617,916 to Bruce A. LeVahn et al include retractor blades clamped to opposite arms of a rigid unitary wishbone-shaped frame for holding back tissue and exposing the internal region at a surgical incision. A clamp secured between the frame and a rigid extension of the operating table allows the frame to be positioned with the arms on either side of the incision. Applicant's copending patent application Ser. No. 07/246,350 discloses an improvement in which the arms are separated to form a "split" wishbone-shaped frame of two support rods joined together by a single clamp adjustable about the table extension. The support rods, being relatively short compared to the unitary frame, permit them to be disassembled and conveniently autoclaved in a standard-size sterilizing tray.

In these and similar structures, the opposed arms or rods are fixed in a relatively widespread position ample for use with retractors on large patients and surgical procedures involving large incisions. However on children and small incisions, the arms of a full-size retractor support are too far apart. Retractor blades with long holders are required to reach the incision, thus reducing the overall rigidity of the retractor system. In addition, the widespread arms with outwardly projecting retractor holders limit the surgeon's physical proximity to a small incision. Conversely, smaller retractor supports suitable for use with children and with small incisions are unsuitable for large patients and larger incisions because the rods and retractor holders get in the way of the surgeon and operating assistants, restricting access to the surgical site. Thus, it is desirable to provide retractor supports in at least two different sizes: one for adults and large incisions, and one for children and small incisions.

Consequently, more versatile retractor apparatus have evolved in which the spread between the support rods is adjustable for various surgical procedures and for different size incisions or patients. These apparatus include clamping devices for fixing a desired amount of spread, but they are very difficult to adjust, and require the assistance of other persons.

SUMMARY OF THE INVENTION

Accordingly, it is an object of the present invention to provide a novel clamp assembly suitable for adjusting the spread between a split wishbone-shaped frame of a surgical retractor apparatus.

Another object of the invention is to provide a single clamp assembly for simultaneously fixing the positions of a pair of retractor support rods relative to each other and to an operating table.

Still another object is to provide a clamp assembly for a pair of rods which can be manipulated and fixed by a single operator at a desired position relative to each other and to a support structure.

A further object of the invention is to provide a clamp assembly for a split wishbone-type frame in which the spread between the opposed arms of the frame can be indexed to one of a plurality of settings.

A still further object is to provide a surgical retractor clamp assembly in which the spread between two retractor support rods is selected from indicia on the clamp, which is easily disassembled for cleaning and sterilizing, and which affords greater versatility for use with various size incisions and patients.

Briefly, these and other objects of the invention are accomplished with a clamp assembly suitable for simultaneously securing surgical retractor support rods of a split wishbone-shaped configuration to each other and to an operating table extension. The clamp assembly includes two independently rotatable clamping disks coaxially stacked on a base and tightened together by a bolt threadingly engaging a T-shaped fitting extending through central openings in the base and disks. Parallel channels in each disk on opposite sides of its opening are formed to receive the proximal ends of the support rods. The base and fitting include aligned bores for receiving the operating table extension. With the bolt and fitting loosely engaged, the base may be rotated about the extension for adjusting the support rods relative to the table, and the disks may be rotated on the base relative to each other for adjusting the spread between the retractor support rods. A pin disposed in one disk registers with holes in the other disk to permit the rods to be indexed at any one of four discrete spread positions. A handle pivotally connected to the bolt provides convenient leverage for simultaneously tightening the support rods in a fixed position relative to each other and to the table extension.

For a better understanding of these and other objects and aspects of the invention, reference will be made to the following detailed description taken in conjunction with the accompanying drawings.

BRIEF DESCRIPTION OF THE DRAWINGS

FIG. 2 is an exploded isometric view of the clamp assembly of FIG. 1;

FIG. 3 is a top plan view of the clamp assembly of FIG. 1 with surgical retractors mounted along the extended portions of the support rods;

FIG. 4 is an elevation view of the clamp assembly of FIG. 1;

FIG. 5 is a fragmentary cross-sectional view of the clamp assembly taken along the line 5—5 of FIG. 4.

DESCRIPTION OF THE PREFERRED EMBODIMENT

Figure 1:
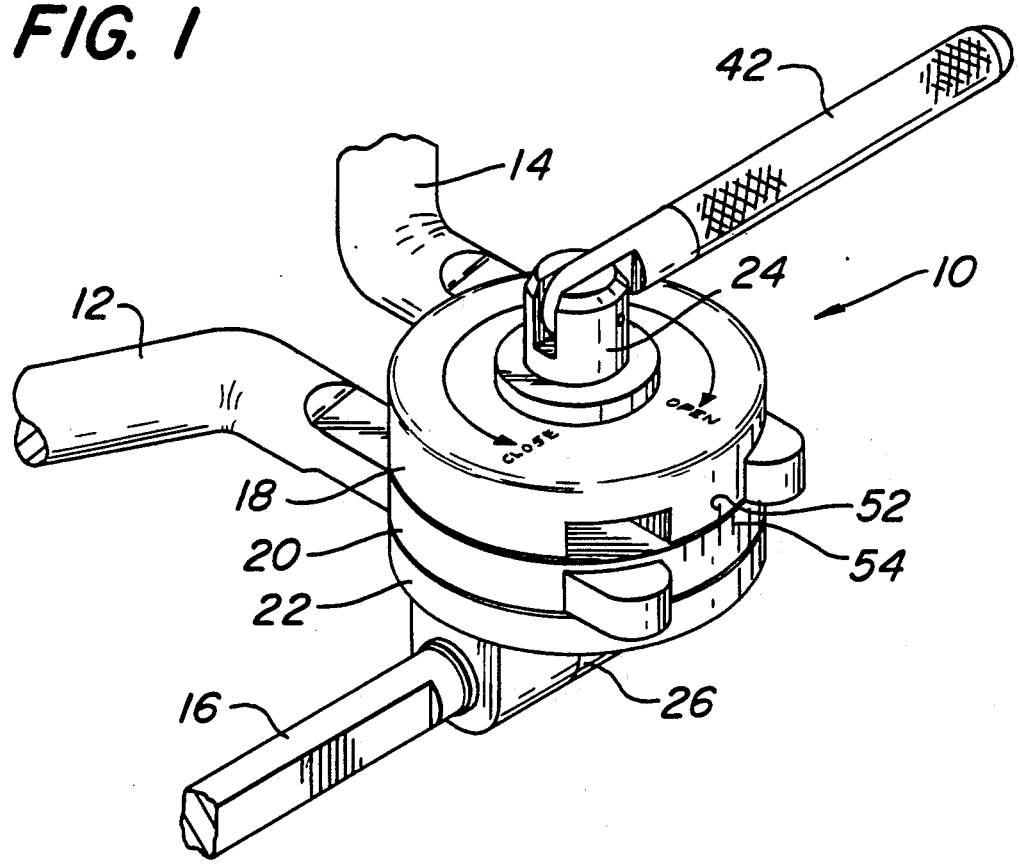
FIG. 1 is an isometric view of the proximal ends of retractor support rods secured to the free end of an operating table extension by a clamp assembly constructed according to the invention.
Figure 6:
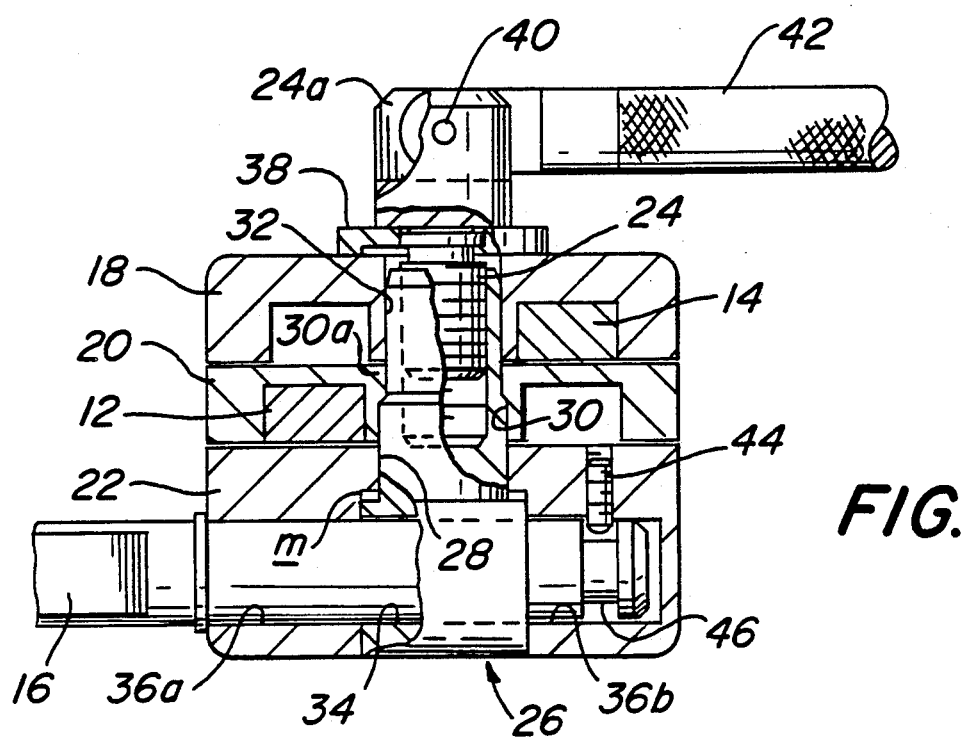
FIG. 6 is a cross-sectional elevation view of the clamp assembly taken along line 6—6 of FIG. 3.

Referring now to the drawings wherein like characters designate like or corresponding parts throughout the several views, there is shown in FIGS. 1-6 a clamp assembly 10 securing a pair of retractor support rods 12 and 14 in a split wishbone configuration to a cylindrical free end of an extension 16 which is rigidly fixed to an operating table (not shown). Assembly 10 includes outer and intermediate clamping disks 18 and 20 coaxially secured on a clamp base 22 by a bolt 24 and a T-shaped fitting 26. Fitting 26 includes a cylindrical stem 26a laterally extending from a tubular collar 26b seated in a recess 22a of base 22 and slidable in coaxially aligned holes 28, 30 and 32 in base 22 and disks 18 and 20, respectively. The diameters of hole 32 and of a rim 30a of hole 30 are less than of hole 28 and correspond to a reduced diameter of the distal end of stem 26a beginning at a shoulder 26c intermediate of the ends in order to ensure proper assembly of disks 18 and 20 on base 22. Collar 26b defines a cylindrical passage 34 alignable with cylindrical passages 36a and 36b in base 22 for slidably receiving the end of extension 16.

Bolt 24 extends from outer clamping plate 20 through a captive thrust washer 38 and terminates with a bifurcated end 24a pivotally connected at a pin 40 to a handle 42 for manually tightening fitting 26 in assembly 10. A clearance m, between recess 22a and collar 26b, allows fitting 26 to be tightened by bolt 24 pressing disks 18 and 20 and base 22 together until passages 34, 36a and 36b are frictionally clamped against rotation on extension 16. A set screw 44 in body 22 extends into bore 36b and engages an annular groove 46 adjacent to the end of extension 16 to prevent removal of extension 16 while allowing assembly 10 to rotate about extension 16 when bolt 24 is loosened.

Clamping disks 18 and 20 further include, respectively, a pair of parallel rectangular channels 48 and 50 facing disk 20 and base 22 on opposite sides of holes 30 and 32 for slidably receiving the proximal ends of rods 12 and 14. The other channel of each disk is unoccupied. The proximal end of each rod has top and bottom flat surfaces interchangeably cooperating with channels 48 and 50 to prevent rotation relative to disks 18 and 20. The distance between the flat surfaces, contiguous with either disks 18 and 20 or disk 20 and base 22, is slightly greater than the depth of channels 48 and 50 to insure proper clamping on rods 12 and 14. That is, as fitting 26 is tightened drawing extension 16 against base 22, rods 12 and 14 are simultaneously clamped in selected ones of channels 48 and 50.

The spread between retractor support rods 12 and 14 may be indexed to one of four positions. A pin 56, press-fitted in disk 18, is radially positioned to register with one of four angularly spaced holes 58 in disk 20. The position of pin 56 is indicated by a cursor 52 and scale 54 inscribed on the side edges of disks 18 and 20, respectively. As illustrated in solid outline in FIG. 3, rods 12 and 14 are shown, with retractors 60, installed in parallel with pin 52 in the second hole 54 from the right (FIG. 5), cursor 52 being aligned with the long or cardinal graduation on scale 54. In a typical embodiment, the spread is about 15 inches at the distal ends of rods 12 and 14. Indexing cursor 52 to the short line to the right of the cardinal graduation causes rods 12 and 14 to "toe-in" with a spread of approximately 12½ inches. Indexing cursor 52 to the short lines on the left of the cardinal graduation produces spreads of 17½ inches and 20 inches.

To utilize the clamp assembly 10 in a retractor support system, fitting 26 is first inserted in base 22 and both are slipped on the free end of operating table extension 16 and restrained from axial movement by extending set screw 44 into groove 46. Disks 20 and 18 are then stacked on base 22, and bolt 24 with washer 38 is loosely threaded into stem 26a. As this occurs, pin 56 registers with the hole 58 associated the desired indexed position of cursor 52 and scale 54. Bolt 24 may now be fully tightened with handle 42 thereby simultaneously clamping assembly 10 to extension 16 and rods 12 and 14 in their respective positions.

Some of the many advantages and novel features of the invention should now be readily apparent. For example, a clamp assembly is provided which is particularly useful with surgical retractor apparatus for adjusting the spread between retractor support rods, which allows operating personnel closer access to the surgical site, and which provide greater use for different size patients and surgical incisions. The assembly enables an operator to fix simultaneously the positions of the support rods relative to each other and to the operating table without the assistance of other persons. The assembly is constructed of relatively few parts which are easily disassembled for cleaning and sterilizing.

It will be understood of course that various changes in the details, steps and arrangement of parts, which have been herein described and illustrated in order to explain the nature of the invention, may be made by those skilled in the art within the principle and scope of the invention as expressed in the appended claims.

I claim:

1. A clamp assembly comprising, in combination:
   a base formed to rotate on a first axis about a first rod;
   an elongate fitting slidably disposed in said base along a second axis normal to said first axis and formed to rotate with said base about the first rod;
   first and second disks slidably disposed on said fitting and independently rotatable about said second axis, one side of said first disk having a channel adjacent to said fitting defining with said base opposed surfaces for clamping a second rod therebetween, and said second disk having a channel adjacent to said fitting defining with the other side of said first disk opposed surfaces for clamping a third rod therebetween; and
   tightening means along said second axis operatively connected to said fitting and said disks for simultaneously fixing the rods relative to each other.

2. A clamp according to claim 1 wherein:
   said base includes an opening along said first axis for slidably receiving the first rod.

3. A clamp assembly according to claim 2 wherein:
   the depth of said channels is less than the thickness of said second and third rods.

4. A clamp assembly according to claim 2 wherein:
   said base includes a recess along the length of said opening; and
   said fitting includes a hole at one end alignable with said opening for receiving the first rod.

5. A clamp assembly according to claim 4 wherein:
   said tightening means includes a shank threadingly engaging the other end of said fitting.

6. A clamp assembly according to claim 1 further comprising:
   indexing means operatively connected to said disks for selecting one of a plurality of angular displacements therebetween, said indexing means includes a plurality of holes in one of said disks disposed to correspond with the angular displacements, and a pin fixed to and extending from the other of said disks for insertion in a selected one of said holes.

7. An improved clamp assembly for a split wishbone surgical retractor apparatus, the apparatus including a pair of retractor support rods having opposed flat sides and an operating table extension having a cylindrical cross section, the improvement comprising:
   a base defining a first passage formed to receive the extension for rotating about said extension on a first axis, and a second passage communicating with said first passage on a second axis normal to said first axis;

an elongate fitting slidably disposed in said second passage having a third passage at one end alignable along the second axis and formed to receive the extension for rotating with said base on said first axis;

a first disk disposed on said fitting and independently rotatable about said second axis, one side of said first disk having a channel adjacent to said fitting forming with said base a fourth passage for receiving one of the rods;

a second disk disposed on said fitting and independently rotatable about said second axis, said second disk having a channel adjacent to said fitting forming with the other side of said first disk a fifth passage for receiving the other of the rods; and tightening means operatively connected to the other end of said fitting and said second disk for simultaneously fixing relative to each other the extension and the rods received in said assembly.

8. A clamp according to claim 7 wherein:
said fourth and fifth passages are of rectangular cross section passage for preventing rotation of said rods.

9. A clamp assembly according to claim 8 wherein:
a depth of said channels of said fourth and fifth passages is less than the thickness across the flat sides of said rods.

10. A clamp assembly according to claim 9 wherein: said fourth and fifth passages are disposed on opposite sides of said fitting.

11. A clamp assembly according to claim 7 wherein:
said tightening means includes a shank threadingly engaging the other end of said fitting.

12. A clamp assembly according to claim 7 further comprising:
indexing means operatively connected to said disks for selecting one of a plurality of angular displacements therebetween, said indexing means includes a plurality of holes in one of said disks disposed to correspond with the angular displacements, and a pin fixed to and extending from the other of said disks for insertion in a selected one of said holes.

13. A clamp assembly comprising, in combination:
a base formed to slidably receive a first rod;
a fitting slidably disposed in said base and formed to be slidable on said first rod;
first and second disks disposed on said fitting for independent rotation about said fitting, one of said disks having a channel on one side adjacent to said fitting forming with said base opposed surfaces for clamping a second rod therebetween and the other of said disks having a channel adjacent to said fitting forming with the other side of said one disk opposed surfaces for clamping a third rod therebetween; and
tightening means operatively connected to said fitting and said other disk for simultaneously securing the three rods relative to each other.

* * * * *